United States Patent [19]

Drizen et al.

[11] Patent Number: 5,079,236

[45] Date of Patent: Jan. 7, 1992

[54] PURE, STERILE, PYROGEN-FREE HYALURONIC ACID FORMULATIONS THEIR METHODS OF PREPARATION AND METHODS OF USE

[75] Inventors: Alan Drizen, Downsview; Anita Aviad, Toronto, both of Canada

[73] Assignee: Hyal Pharmaceutical Corporation, Mississauga, Canada

[21] Appl. No.: 54,859

[22] Filed: May 27, 1987

[51] Int. Cl.$^5$ ............................................. A61K 31/70
[52] U.S. Cl. ...................................... 514/54; 536/55.1
[58] Field of Search ........................... 514/54; 536/55.1

[56] References Cited

U.S. PATENT DOCUMENTS

| | | | |
|---|---|---|---|
| 2,585,546 | 2/1952 | Hadidian | 260/210 |
| 3,396,081 | 8/1968 | Billek | 435/272 |
| 3,862,003 | 1/1975 | Okuyama | 195/7 |
| 4,141,973 | 2/1979 | Balazs | 514/54 |
| 4,303,676 | 12/1981 | Balazs | 514/777 |
| 4,517,295 | 5/1985 | Bracke et al. | 435/101 |
| 4,517,296 | 5/1985 | Sakakibara | 435/119 |
| 4,629,623 | 12/1986 | Balazs et al. | 514/846 |
| 4,782,046 | 11/1988 | Brown et al. | 514/54 |
| 4,801,619 | 1/1989 | Lindblad | 536/55.1 |

FOREIGN PATENT DOCUMENTS

| | | |
|---|---|---|
| 1205031 | 5/1986 | Canada. |
| 0144019 | 6/1985 | European Pat. Off.. |
| 0239335 | 9/1987 | European Pat. Off.. |
| 56-13489 | 8/1981 | Japan. |

OTHER PUBLICATIONS

Gruntova et al., Chemical Abstracts, vol. 76(18):103732p, "Effect of Glycerol and Propylene Glycol on Microbiological ...".

Reddy et al., Chemical Abstracts, vol. 97 (26):222862z, "Effect of Preservatives on the Stability of Oil-in-Water Emulsions."

Cleland, Chemical Abstracts, vol. 76(1972), No. 43075q, "Molecular Weight Distribution in Hyaluronic Acid".

Laurent et al., Chemical Abstracts, vol. 98 (1983), No. 211815f, "The Molecular Weight of Hyaluronic Acid in the Aqueous Lumen ...".

Shimada et al., J. Biochem., vol. 31 (1977), pp. 79–91, "Molecular Weight of Hyaluronic Acid from Rabbit Skin".

Barron et al., *American Journal of Ophthamology, vol. 100 (1985), pp. 377–384.*

The Merck Index, 9th ed., 1976; No. 5972; 755 and 8326.

*Primary Examiner*—John W. Rollins
*Assistant Examiner*—Elli Peselev
*Attorney, Agent, or Firm*—Roper & Quigg

[57] ABSTRACT

A heat stable, purified, pyrogen-free, heat sterilized fraction of hyaluronic acid suitable for use in formulations for intra-articular treatment of animals which includes minor amounts of sulphated mucopolysaccharides, sulphated ash, chlorides, solvents and less than 0.6% protein, having a molecular weight of less than 750,000 and exhibiting a specific absorbance of a 1% solution at A257nm of less than 3. A formulation for intra-articular treatment of animals including an aqueous solution of the heat stable fraction of hyaluronic acid and preservatives, such as sodium benzoate, methylparaben and propylparaben, having a pH of 6.8–8.0 at 25° C. A method of preparing a formulation for intra-articular treatment of animals involving adding and dissolving methyl parahydroxybenzoate, propyl parahydroxybenzoate and sodium benzoate in hot water, mixing the preservative solution to dissolve the parabens, adding sodium hyaluronate in the solution, adjusting the pH of the resultant solution to 6.8–8.0 and diluting with water to a final volume prior to filling suitable dosages for intra-articular treatment of animals into vials which are autoclaved to sterilize the aqueous formulation. An intra-articular treatment involving injecting a suitable dosage of an aqueous solution containing a heat stable, purified, pyrogen-free, heat-sterilized fraction of hyaluronic acid into a joint of an animal suffering from a degenerative joint disease.

4 Claims, No Drawings

PURE, STERILE, PYROGEN-FREE HYALURONIC ACID FORMULATIONS THEIR METHODS OF PREPARATION AND METHODS OF USE

BACKGROUND OF THE INVENTION

1. Field of the Invention

The present invention relates to medically useful preparations based on hyaluronic acid, a naturally-occurring substance found in animal tissue, and especially in rooster comb, vitreous humour, umbilical cords, and synovial fluid of mammals. More particularly, the present invention relates to injectable formulations containing a fraction of hyaluronic acid, which is pyrogen-free, heat stable and has been purified and heat-sterilized. Specifically, the present invention is directed to a heat stable, purified, pyrogen-free, heat-sterilized fraction of hyaluronic acid, formulations and compositions containing such fraction of hyaluronic acid suitable for intra-articular treatment of animals, methods of preparing a formulation containing such fraction of hyaluronic acid suitable for this purpose, and methods for intra-articular treatment of animals with formulations and compositions containing such fraction of hyaluronic acid.

2. Description of Background and Material Information

It is known in the art that hyaluronic acid (HA) has the potential to be a valuable therapeutic agent in the treatment of joint disorders. Introduction of HA into a diseased or malfunctioning joint has the potential to prevent further deterioration of joint function, and even to restore the joint to its normal, healthy condition. Unfortunately, the injection of prior art HA preparations into joint synovial spaces results in serious side-effects in a significant number of cases. The principal side-effects are pain and inflamation of the joint, often impairing normal activity for weeks or months following treatment. Repeated injections of prior art HA preparations may even cause sensitization in the subject, causing progressively more severe side-effects.

Hyaluronic acid (HA) occurs naturally in joint synovial fluid, where it plays a lubricating role, and may have biological activity as well. HA is a mucopolysaccharide, and may alternatively be referred to as a glycosaminoglycan. The repeating unit of the hyaluronic acid molecule is a disaccharide consisting of D-glucuronic acid and N-acetyl-D-glucosamine. Because hyaluronic acid possesses a negative charge at neutral pH, it is soluble in water, where it forms highly viscous solutions. The D-glucuronic acid unit and N-acetyl-D-glucosamine unit are bonded through a glycosidic, beta(1-3) linkage, while each disaccharide unit is bonded to the next disaccharide unit through a beta(1-4) linkage. The beta(1-4) linkages may be broken through hydrolysis with the enzyme hyaluronidase.

A variety of substances, commonly referred to hyaluronic acid, have been isolated by numerous methods from various tissue sources including umbilical cords, skin, vitreous humour, synovial fluid, tumors, haemolytic streptococci pigskin, rooster combs, and the walls of veins and arteries.

Conventional methods for obtaining hyaluronic acid result with a product having differing properties and a wide range of viscosities. U.S. Pat. No. 2,585,546, HADIAN, is an example of a method for obtaining hyaluronic acid which involves extracting acetone-washed umbilical cords with a dilute salt solution, acidifying the resulting extract, removing the clot so formed, precipitating some hyaluronic acid with protein from the acidified extract with ammonium sulfate, agitating the liquid with pyridine, precipitating another fraction highly contaminated with protein, followed by more ammonium sulfate which forces some pyridine out of solution along with the high viscosity hyaluronic acid. The hyaluronic acid collects at the interface between the two liquid phases and may be separated by filtration, centrifugation or other usual procedure. A modification of this process involves the fractionation of the acidic salt extract from umbilical cords with alcohol and ammonium sulfate. Alcohol is added to the acidic salt extract, and the resulting precipitate is removed. Solid ammonium sulfate is added to the liquid until saturation and the solution forms two phases with a precipitate of hyaluronic acid at the interface.

U.S. Pat. No. 3,396,081, BILLEK, produces a dry powder of hyaluronic acid obtained from a source of hyaluronic acid, such as animal organs including the vitreous body of the eye, umbilical cords, and the like, or from bacterial cultures producing hyaluronic acid. A suspension of the resultant dry powder is heated in water for a short time in an alkaline range whereby the protein content is denatured. After adjustment of the optimum pH and temperature range for the enzyme used, the protein is decomposed by proteolytic ferments, preferably by a hydrolase mixture of Aspergillus oryzae. After removing the free amino acids and mineral salts by treatment with ion exchanges, an impure hyaluronic acid solution still containing protein is obtained. The resultant solution of impure hyaluronic acid containing residual protein is then adjusted to an acid pH of about 3-4 in which the impurities form with hyaluronic acid an insoluble complex, while part of the hyaluronic acid itself functions as precipitate for the impurities, particularly for the residual proteins which can otherwise be removed only with difficulty without depolymerization of the hyaluronic acid, whereupon the resulting insoluble complex compounds are separated by high speed centrifuging. After a sodium salt, the resultant hyaluronic acid solution with a concentration of 0.2% in water has a relative specific viscosity of 20 and constitutes a water-clear solution disclosure as being free from proteins, antigens, and pyrogens, which is disclosed as being suitable for heat sterilization without experiencing a considerable drop in viscosity.

U.S. Pat. No. 3,862,003, OKUYAMA et al., is directed to a method of extracting mucopolysaccharides from connective tissues of animals, which involves exposing the connective tissue with water at a temperature of 105°-150° C. under an elevated pressure, subjecting the resultant extract to a protease treatment and/or alkali treatment, and then separating and recovering mucopolysaccharides.

U.S. Pat. No. 4,141,973, BALAZS, is directed to the production of an ultra-pure, high molecular weight hyaluronic acid fraction which is obtained from animal tissue containing hyaluronic acid by a process which involves moving blood from the animal tissue containing hyaluronic acid, extracting hyaluronic acid from the blood, deproteinizing the hyaluronic acid extract, and removing any unidentified inflammation causing agents present therein by treating the deproteinized hyaluronic acid extract at a pH of 6.0-7.0 with a volume of chloroform at least about equal to that of the deproteinized extract, to form a two-phase mixture which is then stirred, sufficiently to insure intimate contact with the two phases at about 15°–40° C., followed by separating out and discarding the chloroform phase.

U.S. Pat. No. 4,517,296, BRACKE et al., is directed to the preparation of hyaluronic acid in high yield from streptococcus bacteria by fermenting the bacteria under anerobic conditions in a $CO_2$ enriched growth medium, separating the bacteria from the resulting broth and isolating the hyaluronic acid from the remaining constituents of the broth. Separation of the microorganisms from the hyaluronic acid is facilitated by killing the bacteria with trichloroacetic acid. After removal of the bacteria cells and concentration of the higher molecular weight fermentation products, the hyaluronic acid is isolated and purified by precipitation, resuspension and reprecipitation.

Despite such prior arts attempts in the preparation of hyaluronic acid, conventional procedures for doing so have been hampered by the need to balance inherently conflicting objectives, i.e., the elimination of inflammatory or pyrogenic properties by extensive purification, and maintaining a high viscosity of the preparation, which generally decreases in response to each successive isolation or purification step. Resolution of this dilemma has been complicated by the fact that the agents responsible for the inflamatory and/or pyrogenic side-effects of the prior art preparations are not well understood, making their efficient elimination extremely difficult.

The present invention overcomes the difficulties of the prior art through the discovery of a hyaluronic acid preparation which contains HA fractions which are heat stable, purified, pyrogen-free and heat-sterilized. Although the HA fractions may have a relatively low molecular weight, the HA fractions are nevertheless highly effective in the treatment of joint disorders while avoiding the side-effects which are a major drawback of the prior art preparations.

SUMMARY OF THE INVENTION

An object of the present invention is to provide a formulation for intra-articular use in animals composed of a solution including a heat-stable, purified, pyrogen-free, heat-sterilized fraction of hyaluronic acid, preferably wherein the hyaluronic acid is present in the form of a salt, such as sodium salt, e.g., sodium hyaluronate, and at least one perservative, preferably selected from the group consisting of sodium benzoate, methylparaben, propylparaben, and combinations of sodium benzoate, methylparaben, and propylparaben.

Another object of the present invention is the provision of a formulation, as described above, including, per milliliter of final solution: about 5 to 20 milligrams of a sodium salt of hyaluronic acid, and about 0.1 to 1.5 milligrams of such a preservative; and preferably about 7.5 to 15 milligrams of the sodium salt of hyaluronic acid, about 0.2 to 1.0 milligrams of sodium benzoate, about 0.05 to 0.15 milligrams of methylparaben, and about 0.02 to 0.1 milligrams of propylparaben; and most preferably about 0.9 to 11 milligrams of the sodium salt of hyaluronic acid, about 0.4 to 0 5 milligrams of sodium benzoate, about 0.8 to 1.2 milligrams of methylparaben, and about 0.4 to 0.06 milligrams propylparaben.

Another further object of the present invention is the provision of a formulation, as described above, including per milliliter of final solution: about 0.9 to 11 milliliters of a sodium salt of hyaluronic acid; about 0.41 to 0.5 milligrams sodium benzoate, about 0.86 to 0.12 milligrams methyl paraben, and about 0.043 to 0.06 milligrams propyl paraben, preferably having a pH within the range of about 6.8–8.0 at 25° C.

It is another object of the present invention to provide a fraction of hyaluronic acid suitable for use in formulations for intra-articular treatment of animals, as described above, wherein the fraction of hyaluronic acid is heat stable, purified, pyrogen-free and heat-sterilized and includes about 0.75 to 1.25% sulphated mucopolysaccharides, about 0.2 to 0.6% protein, about 12.5 to 22.5% sulphated ash, about 3 to 4% chloride, and about 0.2 to 0.6% solvents; and preferably about 1% sulphated mucopolysaccharides about 15 to 19% sulphated ash, about 2% chloride, and about 4% solvents, wherein the solvents are members selected from the group consisting of acetone, ethanol and a mixture of acetone and ethanol, the protein is albumin, and the chloride is sodium chloride.

It is another still further object of the present invention to provide a fraction of hyaluronic acid, as described above, wherein the fraction of hyaluronic acid has an average molecular weight of less than 750,000, preferably less than 500,000, and more preferably wherein the average molecular weight is within the range of 50,000 to 200,000, and most preferably within the range of 75,000 to 150,000.

It is another still further object of the present invention to provide a fraction of hyaluronic acid, as described above, which has a specific absorbance of a 1% solution at $A_{257nm}$ of 1.5 to 3, and preferably about 2.

Another object of the present invention is to provide a method for preparing a formulation for intra-articular treatment of animals which involves providing a purified, heat-sterilized, pyrogen-free stable fraction of hyaluronic acid; filling a mixing tank with hot water; introducing and dissolving preservatives selected from the group consisting of methyl parahydroxybenzoate, propyl parahydroxybenzoate, sodium benzoate and mixtures of methyl parahydroxybenzoate, propyl parahydroxybenzoate and sodium benzoate in the water to form a preservative solution; adding and dissolving the fraction of hyaluronic acid in the preservative solution to form a resultant solution; adjusting the pH of the resultant solution to 6.8–8.0; diluting the pH adjusted solution with an amount of water to a final volume aqueous formulation; filling the aqueous formulation in suitable dosage for intra-articular treatment of animals into vials; and sterilizing the vials containing the aqueous formulation including the fraction of hyaluronic acid.

Another further object of the presnt invention is to provide a method for preparing a formulation, as described above, wherein the preservatives are preferably added sequentially to the heated water in the following order: methyl parahydroxybenzoate, then propyl parahydroxybenzoate, and finally sodium benzoate, and the water has a temperature of about 90° C., wherein the preservative solution is preferably maintained at about 9020 0 C. for 20 minutes while mixing to dissolve the parabens, followed by cooling the preservative solution to about prior to adding the fraction of hyaluronic acid. The sterilizing is performed by autoclaving preferably at a temperature of about 121° C. for about 30 minutes. Adjusting the pH is preferably accomplished by adding appropriate amounts of a pH adjusting agent selected from the group consisting of hydrochloric acid and sodium hydroxide.

Another still further object of the present invention is the provision of a method, as described above, which also involves filtering the final volume of aqueous formulation through a membrane into a receiving vessel prior to filling into the vials, preferably wherein said membrane is a 0.65 micron membrane, and pressurizing the receiving vessel with nitrogen.

It is another object of the present invention to provide a composition for intra-articular treatment of animals composed of a heat stable purified, pyrogen-free, heat sterilized, storage stable fraction of hyaluronic acid, as described above, and a steroid, preferably wherein the fraction of hyaluronic acid and the steroid are present in a ratio of 1:1, and the steroid is methyl prednisolane. The composition also preferably contains a preservative, preferably selected from the group consisting of sodium benzoate, methylparaben, propyl paraben, and mixtures of sodium benzoate, methylparaben, and propyl paraben.

Another further object of the present invention is to provide an intra-articular treatment of animals which involves providing a formulation solution including a heat stable, purified, pyrogen-free, heat-sterilized fraction of hyaluronic acid, preservative, and water in a dosage form containing the fraction of hyaluronic acid in an amount within the range of 10 mg/ml solution to 20 mg/ml solution; and injecting an appropriate dosage of said solution into a joint of an animal suffering from a degenerative joint disease, wherein 5 ml of the solution is injected for carpel, fetlock, coffin and tibotarsal joints, 2.5 ml of the solution is injected for intertarsal and tarsometatarsal joints, 5 ml of the solution is injected into lateral and medial sacs of the femorotibial joint and into the femoropatellar joint, and 10 ml of said solution is injected into the femoropattelar joint.

DETAILED DESCRIPTION

The present invention is, therefore, directed to the provision and use of a purified, pyrogen-free, heat sterilized fraction of hyaluronic acid (HA) and the production of formulations and compositions containing such fraction of HA useful for intra-articular treatment of animals, and particularly horses, which suffer from osteoarthritis, commonly referred to as degenerative joint disease (DJD). Although the present invention is applicable to the treatment of animals of all types, it is found to be particularly effective in the treatment of animals used for sport, and particularly racing, such as race horses which are bred and trained at an early age specifically for racing. For purposes herein, therefore, the following description with respect to the present invention will be given for race horses.

Race horses are particularly susceptible to trauma resulting from training before they are mature which tends to make race horses prone to developing osteoarthritis.

In the past, cortisosteroids have been used to relieve the symptoms of DJD, including pain and inflammation. Notwithstanding any short term alleviation of the symptoms of DJD, treatments with steroids alone often produced major side effects such as ankylosis or the drying of the affected joint.

Subsequently, veterinary medicine began to recognize the benefits derived from injections of hyaluronic acid (HA) into horse joints to relieve symptoms of DJD. Among the advantages was that there were no joint drying effects associated with HA treatment.

One of the first commercial HA products was marketed under the brand name HEALON, manufactured by Pharmacia of Sweden. Despite the noted advantages, and notwithstanding its effectiveness in ameliorating the symptoms of osteoarthritis, the use of HEALON produced a number of adverse side effects, including effusion, heat and pain. Although efforts were made to minimize such side effects by altering the suggested dosages, the problems of side effects continued and remain to this date. The U.S. counterpart HA product of HEALON is HYLARTIN V which is also understood to produce significant adverse side effects in approximately 15% of the horses treated.

The present invention, therefore, is based on the discovery of a fraction of hyaluronic acid (HA) which is both safe and effective in the treatment of osteoarthritis and joint disfunction, and yet does not produce significant side effects in the treated animal. In this regard, a fraction of HA has been developed which is extremely heat stable so as to permit its purification to a very high degree thereby making it essentially pyrogen-free and eliminating the inherent inflammatory properties of the HA molecule.

The heat stable fraction of HA used for purposes of the present invention is prepared into a formulation having a dosage suitable for intra-articular treatment of animals. Preferably, a salt of HA is first produced for this purpose, for example by combining the fraction of HA with sodium carbonate or sodium bicarbonate. Alternatively, sulphated hyaluronic salts, as well as homologs and analogs thereof, may be used for purposes preparing of the formulation. The HA fraction suitable for the intra-articular treatment of animals is combined with effective anti-microbial agents, such as sodium benzoate and parabens, to produce a dosage form which does not result in adverse side effects or reactions and yet is highly effective in the management of osteoarthritis and degenerative joint disease.

The fraction of hyaluronic acid suitable for purposes of the present invention has been analyzed as also containing about 1% sulphated mucopolysaccharides, about 0.4% protein, about 15-19% sulphated ash, about 2% chlorides, and about 0.4% residual solvents. The solvents are members selected from the group consisting of acetone and ethanol used to extract the HA fraction from the tissue source, which is preferably rooster combs. The chloride content of the fraction of HA is sodium chloride. The protein present in the fraction of HA is expressed as a percentage of albumin as determined by the Lowry test. The fraction of HA in accordance with the present invention also exhibits a specific absorbance of about 2.0. The fraction of HA in accordance with the present invention has been determined to have an average molecular weight of less than about 750,000, and preferably less than 500,000, and most preferably has average molecular weight falling within the range of 75,000-150,000.

The procedure for manufacturing the dosage form of the aqueous formulation will now be described. As in the manufacture of any pharmaceutical or medicinal product, it is extremely important that metal equipment and utensils be made of stainless steel and that all equipment and implements be cleaned and sterilized prior to beginning the manufacturing process. Initially, water is added into a stainless steel tank which is heated to a temperature of about 90° C. A high speed mixer is then inserted into the heated water. A preservative solution is first formed in the tank by adding and dissolving methyl parahydrooxybenzoate, propyl parahydrooxybenzoate, and sodium benzoate in that order in the hot water. The preservative solution is then maintained at a temperature of 90° C. for twenty minutes during mixing to dissolve the parabens. Subsequently, the preservative solution is cooled to 25° C. at which time sodium hyaluronate is added to the cooled preservative solution while mixing to dissolve the sodium hyaluronate. Once this is accomplished, the resultant sodium hylauronate solution is then adjusted to a pH of 6.8-8.0 by adding appropriate amounts of sodium hydroxide or hydrochloric acid. The pH adjusted solution is then diluted with sufficient quantities of water to form a final volume of the aqueous formulation suitable for intra-articular treatment of animals and mixed for ten minutes. The aqueous formulation is then filtered through a 0.65 micron sterile membrane into a sterile stainless steel receiving vessel, preferably pressurized with nitrogen gas. The aqueous formulation in appropriate dosage is then filled into sterilized 5 ml-1 borosilicate glass vials which are stopped with rubber stoppers and sealed with aluminum lacquered flip-off seals. The sealed vials containing the aqueous formulation in accordance with the present invention are subsequently sterilized in an autoclave at a temperature of 121° C. for thirty minutes.

The aqueous formulation produced in accordance with the above methodology is a clear, colorless, slightly viscous aqueous solution which has no visible particulate matter present when viewed against dark and light backgrounds. The sterility of the aqueous formulation meets the requirements of USP XX1, 1985, p 1351. The pyrogen content meets the requirements of USP XX1, p 1181, i.e., for the absence of pyrogens using contents of one vial per rabbit. The pH of the product at 25° C. is within the range of 6.8-8.0. The preferred dosage form is a 5 ml single dose vial.

The dosage form of the aqueous formulation thus contains a heat stable fraction of HA which allows for a high degree purification and permits the aqueous formulation to be terminally heat-sterilized. In addition, the dosage form of the aqueous formulation contains an effective antimicrobial preservative system. Thus, the dosage form of the aqueous formulation in accordance with the present invention is extremely storage stable over a wide range of temperatures, including temperatures as high as 86° F., for at least three years. In addition, although the aqueous formulation is storage stable for extended periods of time at temperatures within the range of about 35° F. and 86° F., the aqueous formulation can be exposed to temperatures of up to 100° F. and below freezing and yet still function without adversely affecting the performance of the product.

Preferably, the aqueous formulation containing the HA fraction in accordance with the present invention is supplied both in single dose vials containing 5 ml (50 mg) of a 10 mg/ml solution of sodium hyaluronate, and in multidose vials containing 5 ml (100 mg) of a 20 mg/ml solution of sodium hyaluronate, and also contains 0.45 mg sodium benzoate, 0.096 mg methyl paraben and 0.048 mg propyl paraben as preservatives.

The preferred dose of the aqueous formulation containing the HA fraction in accordance with the present invention is 5 ml/50 mg. This dose has been found to be the most appropriate dose for all joints, including the hock and stifle joints. In most cases, only a single injection of 5 ml of the aqueous formulation containing the HA fraction in accordance with the present invention is required to effectively treat hocks. A more preferred dose of the aqueous formulation containing the HA fraction in accordance with the present invention is 50 mg intra-articularly for carpal fetlock coffin and tibiotarsal joints. The intertarsal joints and tarsometatarsal joints should be injected with 25 mg of the aqueous formulation. For the stifle, 50 mg of the aqueous formulation should be injected into the lateral and medial sacs of the femorotibial joint and into the femoropatellar joint. It is preferred, however, to inject 100 mg of the aqueous formulation into the femoropatellar joint to eliminate the need to inject the medical sac.

As in all injection procedures, strict aseptic procedures should be followed for the intra-articular injection of the aqueous formulation containing the HA fraction in accordance with the present invention. In this regard, the site should be free of dirt, hair, and topical medication including soapy residues. Following injection, a sterile dressing and bandage should be applied as appropriate for the injected site.

In addition, the aqueous formulation containing the HA fraction in accordance with the present invention may also be physically combined with steroids, and preferably methyl prednisolone, i.e., Depo-medrol. It has been found that the combination of the aqueous formulation in accordance with the present invention and Depo-medrol produces a homogenous suspension which is of major benefit in the treatment of a number of inflammatory disorders.

Related to this, it is also believed that the combination of the aqueous formulation containing the HA fraction in accordance with the present invention and methyl prednisolone can be of significant benefit in pre-race or pre-event conditions which require fast relief of osteoarthritic symptoms, including pain and inflammation. In this regard, the incidence of serious side effects from the steroid is reduced by the presence of the aqueous formulation containing the HA fraction in accordance with the present invention. Another use for the combination of the aqueous formulation of the present invention and methyl perednisolone is injection into tendon sheaths. To this end, a 2 cc dosage of a combination of an aqueous formulation containing the HA fraction in accordance with the present invention and a steroid in a ratio of 1:1 may be injected over the entire enlargement in tendon inflammation.

Although not wishing to be bound to any particular theory, it is believed that exogenous injected HA helps restore hemeostasis in the joint through mechanisms which at present are not clearly understood. It is believed, however, that injected HA normalizes the synovial fluid by relieving the synovial membrane of its metabolic demands. The HA may also exert an important effect on the cartilage matrix and the catabolic enzymes released in the inflamed joint. Although the exact mechanism of the therapeutic action of HA have not been fully identified, the effectiveness of the treatment has been established, as discussed in more detail with respect to the following tests. In brief, results of clinical studies involving the injection of the aqueous formulation containing the fraction of hyaluronic acid in accordance with the present invention into joints of race horses have shown a reduction in pain, improvement in joint mobility, with no apparent deleterious effects on the joint and no apparent systemic reaction in the horse. Post-surgical injection of the aqueous formulation containing the fraction of hyaluronic acid in accordance with the present invention has been found to increase healing and reduce the convalescence.

The following tests are presented to show the effectiveness of the heat stable, pure, pyrogen-free, heat sterilized fraction of hyaluronic acid as used in accordance with the present invention, which is referred to in these tests as Synacid.

TESTS

I. Synacid Efficacy

1. Dose Response Study

The purpose of the study was to determine the optimal therapeutic dose of Synacid.

An adjuvant carpitis model was used to assess the efficacy of four different doses of Synacid (5, 20, 50, and 75 mg) and of two control treatments (saline placebo and a positive active drug control, Hylartin V). Hylartin V was administered at its recommended therapeutic dose.

The arthritic model was induced with a single intra-articular injection of Freund's Adjuvant into the carpal joint using standard aseptic technique. This carpitis model is characterized by:

i) inflammation of the synovial membrane, exudation into the joint cavity, lameness and periarthritis, and is, therefore, compatible with the intended use of Synacid;

ii) a syndrome which is uniform and persistent for the duration of the study, permitting practical group sizes;

iii) parameters which lend themselves to quantitative evaluation of the treatment response, i.e., joint circumference, stride length, and angle of flexion; and iv) characteristics which provide for confirmation of the syndrome, e.g., joint fluid.

Thirty-six healthy mature horses of Quarterhorse type served as the experimental animals. There were 17 geldings, 18 mares, and 1 stallion, ranging in age from 2 to 6 years and weighing from 796 lbs to 1016 lbs. Animals were acclimated to the environment over a 10 day period, maintained in covered stalls and fed a routine weight maintenance ration with hay and water ad libitum. Animals were randomly allocated to one of the six treatment groups, and the study was run in 3 replicates of 12 animals, with each treatment dosage being equally represented. Therefore, six animals were tested at each dosage.

Model induction occurred following the 10 day acclimation period. A single treatment with the assigned drug dosage was administered five days after model induction.

Observations were made prior to model induction, prior to treatment, and for 4 weeks post-treatment consisting of:

a) temperature, pulse and respiration (daily);
b) lameness evaluation (weekly) including:
 i) angle of flexion of carpus at rest,
 ii) maximum angle of flexion permitted,
 iii) length of stride of lame limb after resting,
 iv) length of stride of lame limb following exercise,
 v) lameness score,
 vi) pain on palpation of the affected joint,
 vii) hyperthermia (heat) of the affected joint;
c) radiocarpal joint circumference (weekly);
d) carpal volume measurements (prior to treatment and at the conclusion of the study);
e) synovial fluid analysis of protein content (weekly); and
f) hemogram (weekly).

Table 1 shows that prior to model induction, the test animals were sound and similar (normal) in their response parameters.

TABLE 1

Means of Lameness Related Variables of the Animals in the 20 mg, 50 mg and 75 mg Synacid Dose Groups Before Model Induction

| Dose Group | Flex Rest | Flex Max | Strd Rest | Strd Exer | Jt Circ | Lameness |
|---|---|---|---|---|---|---|
| 20 mg Synacid | 0.00 | 120.00 | 62.20 | 62.70 | 11.50 | 0.00 |
| 50 mg Synacid | 0.00 | 118.00 | 62.30 | 62.30 | 11.63 | 0.00 |
| 75 mg Synacid | 0.00 | 118.00 | 61.50 | 62.00 | 11.42 | 0.00 |

Flex Rest  flexion of carpus at rest, in degrees
Flex Max  maximum flexion permitted on manipulation, in degrees
Strd Rest  stride length at walk after rest, in inches
Strd Exer  stride length at walk after standardized exercise, in inches
Jt Circ  circumference of affected radiocarpal joint, in inches
Lameness  numerical score from 0 (sound) to 3 (severely lame)

The severity and uniformity of the induced arthritis model is apparent from the values in Table 2 which indicate severe lameness, i.e., a score of 3; lack of weight bearing, i.e., flexion at rest; restriction in ability to fully flex affected limb, i.e., maximum flexion permitted; decreased stride length; and increased joint circumference which reflects the presence of swelling.

TABLE 2

Means and Lameness Related Variables of the Animals in the 20 mg, 50 mg and 75 mg Synacid Dose Groups 5 Days After Model Induction and Immediately Prior to Treatment

| Dose Group | Flex Rest | Flex Max | Strd Rest | Strd Exer | Jt Circ | Lameness |
|---|---|---|---|---|---|---|
| 20 mg Synacid | 11.67 | 56.67 | 46.00 | 44.00 | 13.17 | 2.83 |
| 50 mg Synacid | 11.67 | 60.00 | 49.00 | 46.83 | 13.04 | 2.83 |
| 75 mg Synacid | 11.67 | 59.17 | 50.17 | 48.50 | 12.75 | 3.00 |

Flex Rest  flexion of carpus at rest, in degrees
Flex Max  maximum flexion permitted on manipulation, in degrees
Strd Rest  stride length at walk after rest, in inches
Strd Exer  stride length at walk after standardized exercise, in inches
Jt Circ  circumference of affected radiocarpal joint, in inches
Lameness  numerical score from 0 (sound) to 3 (severely lame)

At the end of the study a statistical analysis (ANOVA and Duncan's Multiple Range Test) was performed to test for dose effect. The results showed that the six different treatment dosages consistently fell into two distinct groups. The first consisting of the saline placebo, 5 mg Synacid and 20 mg Synacid; the second group consisting of 50 mg Synacid, 75 mg Synacid and 20 mg Hylartin V. These two groups were significantly ($p < 0.001$) different in clinical response, but dosages within each group were not different than each other ($p > 0.05$). This is considered highly meaningful. The possibility that this low p-value (0.0001) occurred by change is less than one in ten thousand.

One week after treatment, improvement was evident in the 50 mg Synacid, 75 mg Synacid and Hylartin V treatment groups in the following response parameters:

i) flexion at rest,
ii) maximum flexion permitted,
iii) stride length at rest and after exercise,
iv) lameness,
v) hyperthermia (joint heat),
vi) pain on palpation, and
vii) respiration rate.

Table 3 demonstrates that the improvement in lameness related variables at one week following treatment was comparable in the 50 mg and 75 mg Synacid groups. Improvement also occurred in the 20 mg Synacid group but to a significantly lesser extent.

TABLE 3

Means of Lameness Related Variables of the
Animals in the 20 mg, 50 mg and 75 mg Synacid
Dose Groups One Week After Treatment (day 7)

| Dose Group | Flex Rest | Flex Max | Strd Rest | Strd Exer | Jt Circ | Lameness |
|---|---|---|---|---|---|---|
| 20 mg Synacid | 10.00 | 61.67 | 51.67 | 50.33 | 13.63 | 2.50 |
| 50 mg Synacid | 0.00 | 82.50 | 59.67 | 60.17 | 13.29 | 1.00 |
| 75 mg Synacid | 0.00 | 80.00 | 59.83 | 60.83 | 12.92 | 1.00 |

Flex Rest — flexion of carpus at rest, in degrees
Flex Max — maximum flexion permitted on manipulation, in degrees
Strd Rest — stride length at walk after rest, in inches
Strd Exer — stride length at walk after standardized exercise, in inches
Jt Circ — circumference of affected radiocarpal joint, in inches
Lameness — numerical score from 0 (sound) to 3 (severely lame)

At three weeks after treatment joint circumference was also significantly reduced in the 50 mg and 75 mg Synacid groups and in the active control group when compared to the placebo, 5 mg, and 20 mg Synacid groups.

A return to pre-model induction values for most lameness related variable was evident at 4 weeks in all but the 5 mg, 20 mg Synacid, and placebo dosage groups.

Table 4 provides the data from the 4 week post-treatment evaluation.

TABLE 4

Means of Lameness Related Variables of the
Animals in the 20 mg, 50 mg and 75 mg Synacid
Dose Groups 4 Weeks After Treatment (day 28)

| Dose Group | Flex Rest | Flex Max | Strd Rest | Strd Exer | Jt Circ | Lameness |
|---|---|---|---|---|---|---|
| 20 mg Synacid | 6.67 | 63.33 | 53.33 | 53.17 | 13.88 | 2.00 |
| 50 mg Synacid | 0.00 | 90.00 | 61.83 | 62.50 | 12.75 | 0.00 |
| 75 mg Synacid | 0.00 | 90.83 | 62.00 | 62.67 | 12.79 | 0.17 |

Flex Rest — flexion of carpus at rest, in degrees
Flex Max — maximum flexion permitted on manipulation, in degrees
Strd Rest — stride length at walk after rest, in inches
Strd Exer — stride length at walk after standardized exercise, in inches
Jt Circ — circumference of affected radiocarpal joint, in inches
Lameness — numerical score from 0 (sound) to 3 (severely lame)

The 50 mg Synacid does group was statistically equivalent to the Hylartin V control group at all evaluation periods with respect to the resolution of the inflammation induced by the model.

A comparison of the lameness related variables in these groups is provided in Table 5.

TABLE 5

Means for Lameness Related Variables of the
Animals in the 50 mg Synacid Dose Group
and the 20 mg Hylartin V Control Group

| Evaluation Before Model | Flex Rest | Flex Max | Strd Rest | Strd Exer | Jt Circ | Lameness |
|---|---|---|---|---|---|---|
| Induction | | | | | | |
| 50 mg Synacid | 0.00 | 118.00 | 62.30 | 62.30 | 11.63 | 0.00 |
| Hylartin V | 0.00 | 118.00 | 62.00 | 62.80 | 11.63 | 0.00 |
| Before Treatment | | | | | | |
| 50 mg Synacid | 11.67 | 60.00 | 49.00 | 46.83 | 13.04 | 2.83 |
| Hylartin V | 10.83 | 60.83 | 49.17 | 47.00 | 13.54 | 3.00 |
| One Week After Treatment | | | | | | |
| 50 mg Synacid | 0.00 | 82.50 | 59.67 | 60.17 | 13.29 | 1.00 |
| Hylartin V | 0.83 | 82.50 | 59.00 | 59.83 | 13.33 | 1.17 |
| Four Weeks After Treatment | | | | | | |
| 50 mg Synacid | 0.00 | 90.00 | 61.83 | 62.50 | 12.75 | 0.00 |

TABLE 5-continued

Means for Lameness Related Variables of the
Animals in the 50 mg Synacid Dose Group
and the 20 mg Hylartin V Control Group

| Evaluation Before Model | Flex Rest | Flex Max | Strd Rest | Strd Exer | Jt Circ | Lameness |
|---|---|---|---|---|---|---|
| Hylartin V | 0.00 | 83.33 | 61.83 | 62.33 | 13.25 | 0.17 |

Flex Rest — flexion of carpus at rest, in degrees
Flex Max — maximum flexion permitted on manipulation, in degrees
Strd Rest — stride length at walk after rest, in inches
Strd Exer — stride length at walk after standardized exercise, in inches
Jt Circ — circumference of affected radiocarpal joint, in inches
Lameness — numerical score from 0 (sound) to 3 (severely lame)

No significant differences as a result of treatment with any of the six dosage groups were found for body temperature, pulse rate, white blood cell counts and red blood cell counts. The absence of change in these parameters provides evidence for the safety of all dosage levels administered.

Also, no significant differences in synovial fluid protein were found among the six dosage groups studied. In each case, including saline placebo, synovial fluid protein levels declined progressively thus making it difficult to detect dose group effects.

2. Force Plate Efficacy Study

The therapeutic effectiveness of Synacid was investigated in 22 naturally occurring cases of equine osteoarthritis, using the Standing Force Plate as an objective and quantitative measure of lameness.

The standing force plate measures fluctuations in weight bearing of one limb at a time. Fluctuations in the ability of a leg support weight with a constant force pressure are computed in the form of a histogram with a resultant relative standard deviation, or FPU. The lower the FPU, the sounder the limb, indicating that it can support weight evenly. The higher the FPU, the lamer the limb, indicating instability in weight bearing which is caused by pain when a sore leg is in support. Lameness is also evaluated by comparison of the FPU of the affected leg and the contralateral normal leg which serves as a control.

Front limbs are tested by having the horse stand quietly with the test leg centered over the plate, and the contralateral front leg held up. Each leg is tested 4 times, and on each test day both front limbs are evaluated.

The horses in this study has lameness in one front limb only, and in either the carpus or the fetlock joint only. Twenty-four horses participated in all. Four served as untreated controls, two of which were subsequently treated and re-evaluated on the force plate. Therefore twenty-two horses were evaluated prior to Synacid treatment and for 3 weeks following treatment.

Treatments consisted of a single intra-articular injection of 50 mg of Synacid.

There were 23 Standardbreds and 1 Thoroughbred, 16 geldings, 6 females and 2 males, ranging in age between 2 and 13 years. Diagnosis was based on clinical examination, force plate measurements, radiographs and in 8 cases on desensitization of the affected joint. Twenty-two horses were in active training or racing and 2 horses were in light training only. Fourteen horses were treated for carpal joint dysfunction and 10 for front fetlock joint disease.

The breakdown of joints treated in summarized in Table 6.

TABLE 6

Pivotal Force Plate Efficacy Study:
Distribution of Joints Treated

| Joint | Left | Right | Total |
|---|---|---|---|
| Carpus | 5 | 9 | 14 |
| Front Fetlock | 7 | 3 | 10 |
| TOTAL | 12 | 12 | 24 |

Five of the horses with right carpal lameness were treated in both the radiocarpal and intercarpal joint spaces, and two horses with left carpal involvement received radiocarpal and intercarpal joint injections. Therefore, in the 14 horses with carpal joint arthritis, 12 intercarpal joints and 9 radiocarpal joints were treated, as illustrated in Table 7.

TABLE 7

Pivotal Force Plate Efficacy Study:
Distribution of Carpal Joint Treatments

| Side | RC | IC | RC & IC |
|---|---|---|---|
| Left | 0 | 3 | 2 |
| Right | 2 | 2 | 5 |
| TOTAL | 2 | 5 | 7 |

RC  Radiocarpal joint
IC  Intercarpal joint
RC & IC  Both radio- and intercarpal joints

Observations

Radiographs were taken prior to Synacid treatment. Most horses had evidence of degenerative joint disease of mild to moderate severity. Only one horse had clinical carpitis with no radiographic lesions.

Synovial fluid samples were taken pre-treatment and at the end of the evaluation period.

Force Plate assessments were made before treatment and at days 5, 10, 15 and 20 post-treatment, or at 4, 8, 12, 16 and 20 days. Clinical assessments were also made at each evaluation period.

Eight of the horses were injected intra-articularly with a local anesthetic after their pre-treatment force plate assessment but prior to Synacid treatment. Force plate measurements were repeated when the joint was desensitized.

Results

Sound (control) limb readings on the force plate remained much the same throughout the evaluation period. Unsound limbs had significantly higher FPU values (2.5668) than sound control limbs (1.4785) prior to Synacid treatment. A significant reduction ($p<0.01$) in FPU of the treated limbs was apparent by the first visit following Synacid treatment, when the FPU of treated limbs had decreased from 2.5668 to 1.7473. The mean FPU of treated limbs continued to decrease progressively following Synacid treatment and by the 5th and 6th visits (16 and 20 days after Synacid treatment), the FPU of treated limbs (1.3110) was statistically the same as the control limbs (1.3302).

The mean FPU values of the sound and unsound limbs of the 22 horses treated is provided in Table 8.

TABLE 8

Pivotal Force Plate Efficacy Study:
Mean FPU of 22 Synacid Treated Horses

| Day of Visit | Control or Sound Legs | Unsound, Treated Legs |
|---|---|---|
| 0 | 1.4785 | 2.5668 |
| 4 days | 1.3982 | 1.7473 |
| 8 days | 1.3791 | 1.5230 |
| 12 days | 1.3026 | 1.3994 |
| 16 days | 1.4358 | 1.4201 |
| 20 days | 1.3302 | 1.3110 |

0 = Pre-injection
4-20 = Post-injection

The four untreated control horses had similar FPU values as the main group of horses: sound limbs had a mean FPU of 1.2994, compared to 2.4177 in unsound limbs. During the 3 week no treatment evaluation period, the FPU values of the unsound limbs did not decrease, and was 2.5129 at the end of 3 weeks. The two control horses which were subsequently treated with Synacid and evaluated for another 3 week period, did show significant reduction in the FPU of their unsound limbs following treatment.

This data is summarized in Table 9.

TABLE 9

Pivotal Force Plate Efficacy Study:
Mean FPU of Control Horses

| Evaluation | Visit Days | Sound Legs | Unsound Legs |
|---|---|---|---|
| No | 0 | 1.2994 | 2.4177 |
| Treatment | 5-7 days | 1.2612 | 2.4555 |
| Phase | 9-11 days | 1.2571 | 2.4956 |
| (n = 4) | 19-21 days | 1.2536 | 2.5129 |
| Treatment | 0 | 1.2943 | 2.5845 |
| Phase | 4 days | 1.2665 | 1.7515 |
| (n = 2) | 8 days | 1.2645 | 1.6409 |
|  | 12 days | 1.2142 | 1.4715 |
|  | 16 days | 1.1641 | 1.1866 |
|  | 20 days | 1.4780 | 1.1602 |

0 = Pre-injection
4-20 = Post-injection

Theses results indicate that the improvement in lameness during the three week study period was attributable to Synacid treatment, as lack of training alone did not cause FPU values and lameness to decrease.

The effect of intra-articular anesthesia on lame joints (prior to Synacid treatment) was to significantly reduce the FPU values. FPU values of anesthetized unsound limbs became statistically equivalent to the FPU values of the contralateral controls. This procedure showed that the FPU is a sensitive measurement of the amount of lameness present and that FPU decreases when the limb becomes sounder. Therefore, the Synacid treatment had the same effect in 3 weeks as the intra-articular anesthetic.

Table 10 shows the effect of the intra-articular anesthetic of the lame limbs for the 8 horses who underwent this procedure.

TABLE 10

Pivotal Force Plate Efficacy Study:
Effect of Intra-Articular Anesthesia of Lame Joint FPU

| Horse | Lame Limb FPU Pre-Anes.+ | Lame Limb FPU Post-Anes.+ | Sound Limb FPU+ |
|---|---|---|---|
| 1 | 2.0337 | 1.6685 | 1.5886 |
| 2 | 1.8521 | 1.2773 | 1.2016 |
| 3 | 2.3454 | 1.4152 | 1.4690 |
| 4 | 2.4825 | 1.1723 | 1.3024 |
| 5 | 2.0170 | 1.2823 | 1.2228 |
| 6 | 2.5311 | 1.1913 | 1.2372 |
| 7 | 2.6063 | 1.3158 | 1.3017 |

TABLE 10-continued

Pivotal Force Plate Efficacy Study:
Effect of Intra-Articular Anesthesia of Lame Joint FPU

| Horse | Lame Limb FPU | | Sound Limb FPU+ |
|---|---|---|---|
| | Pre-Anes.+ | Post-Anes.+ | |
| 8 | 2.5190 | 1.2953 | 1.2090 |
| Mean | 2.2981 | 1.3272 | 1.3165 |

+ each value is the mean FPU of 4 readings
Anes = intra-articular anesthetic

The clinical assessments of lameness correlated closely with the FPU values obtained on the force plate. A substantial alleviation of lameness and of other clinical signs of joint inflammation such as heat, effusion and pain on flexion, was evident at the first evaluation following Synacid treatment. No untoward effects of Synacid injection occurred in any of the horses. One horse experienced a transient increase in heat and soreness 2 days after injection, which did not interfere with a successful outcome of treatment.

The response to treatment was considered to be sub-satisfactory in only one horse, although substantial improvement was evident compared to pre-treatment, as reflected by decreasing FPU and clinically.

Synovial fluid analysis did not correlate well with degree of lameness, nor with radiographic abnormality. However, in the case of the nine joints in this study which had elevated (>10 mg/ml) protein values, seven returned to normal (<10 mg/ml) following Synacid treatment.

3. Positive Controlled Field Study

The purpose of this study was to compare the efficacy of the new drug, Synacid, with the efficacy of Hylartin V, a related drug.

The study was conducted in three separate geographical centres. All three study locations admitted Thoroughbred race horses only, and treated carpal joints only. Diagnosis of carpal joint dysfunction was based on clinical and radiographic examination and in some cases on intra-articular anesthesia of the joint.

Horses received either 50 mg Synacid or Hylartin V as a treatment, according to a pre-determined computer generated randomization sequence. Both treatments were administered intra-articularly at their respective recommended therapeutic doses.

At the initial visit, horses were evaluated as per the following inclusion criteria:
1. Unilateral lameness of carpal joint origin.
2. Duration of lameness less than or equal to 3 months.
3. Detailed medical histories available.
4. No orthopedic surgery within the previous 4 months.
5. No intra-articular corticosteriod treatment in the preceding 60 days.
6. Lameness visually detectable at the jog.
7. Actively training or racing.
8. No slab fractures.
9. 2-5 year old horses.

Only horses which fit these requirements were admitted into the study.

The study duration was two weeks, with 5 post-treatment follow-up visits at 1, 3, 5, 7, and 14 days. The key follow-up visits with respect to drug efficacy were at 7 and 14 days. The focus of the 1, 3, and 5 day post-treatment visits was to evaluate drug safety.

A repeat treatment at the one week visit was optional depending on response.

Observations

Observations were made on joint heat, joint effusion, joint circumference, pain response on passive joint flexion, pain response on joint palpation and lameness grade. Data recording was made objective and uniform among the study centres by providing numerical scoring systems and by establishing anatomical landmarks for joint circumference measurements. Heat and pain responses to flexion and palpation were standardized by comparison with the contralateral sound limbs.

The numerical codes used were as follows:

| | |
|---|---|
| Heat 0 = | absent; |
| 1 = | slight; |
| 2 = | mild; |
| 3 = | moderate; |
| 4 = | severe. |

Heat evaluations were based on the difference between the sound carpus and the lame carpus, and were made prior to exercise.

| Effusion | 0 = absent; |
|---|---|
| | 1 = detectable on careful palpation of the joint; |
| | 2 = obvious joint capsule distension; |
| | 3 = severe joint capsule distension grossly visible at a distance. |
| Lameness Grade | 0 = sound, no detectable lameness; |
| | 1 = slight lameness, detectable by an expert only; |
| | 2 = lameness observed at a jog and consistently apparent under certain circumstances such as weight-bearing, circling; |
| | 3 = lameness observed under all circumstances, and at the walk; |
| | 4 = three-legged lameness or minimal weight-bearing. |

Subjective assessments were also made regarding improvement in performance and overall response to treatment.

Data from each study centre was analyzed separately and then combined for a composite analysis. This discussion is confined to the composite analysis.

Results

Fifty-eight horses were treated in the study, with 30 having received Synacid and 28 having received Hylartin V.

Table 11 lists the demographic and medical history variables of the horses.

TABLE 11

Positive Controlled Field Study:
Demographic and Medical History Variables

| Variables | Synacid n = 30 | Hylartin V n = 28 | Statistical Comparison |
|---|---|---|---|
| Sex: | | | |
| female | 12 | 15 | |
| male | 9 | 5 | n.s. |
| gelding | 9 | 8 | |
| Mean age: (years) | 3.1 | 2.8 | n.s. |
| Race winners | 11 | 10 | |
| Non winners | 16 | 17 | n.s. |
| Duration of lameness | | | |
| 2 weeks | 12 | 12 | |

TABLE 11-continued

Positive Controlled Field Study:
Demographic and Medical History Variables

| Variables | Synacid n = 30 | Hylartin V n = 28 | Statistical Comparison |
|---|---|---|---|
| 2 weeks-3 months | 18 | 16 | n.s. |
| Onset of lameness: | | | |
| acute | 19 | 16 | |
| insidious | 11 | 12 | n.s. |
| Joint treated: | | | |
| intercarpal | 21 | 22 | |
| radiocarpal | 13 | 9 | n.s. | n.s. = nonsignificant; p > 0.05

The statistical comparison column in Table 11 shows that the Synacid and Hylartin V treated horses were statistically equivalent with respect to the variables on medical history. These comparisons were made using Fisher's exact test except for age where analysis of variance was used.

A statistical analysis on joint heat, joint effusion, joint circumference and lameness grade prior to drug administration also revealed no difference between the Synacid and Hylartin V groups. Therefore, post-treatment comparisons between the two drug groups are valid since the starting points are established as equivalent.

The mean values of these parameters are presented in Table 12, along with the statistical comparison (based on analysis of variance) of the treatment groups.

TABLE 12

Positive Controlled Field Study:
Clinical Parameters Prior to Treatment

| Parameter | n = 30 Synacid | n = 28 Hylartin V | Statistical Comparison |
|---|---|---|---|
| Heat | 2.0 | 1.8 | n.s. |
| Effusion | 1.7 | 1.7 | n.s. |
| Jt Circ. RC | 32.48 | 32.90 | n.s. |
| Jt Circ. IC | 30.72 | 30.23 | n.s. |
| Lameness Grade | 2.5 | 2.4 | n.s. |

Jt Circ. RC = Radiocarpal joint circumference, in centimeters, of abnormal joints
Jt Circ. IC = Intercarpal joint circumference, in centimeters, of abnormal joints
n.s. = nonsignificant, p > 0.05

The data collected at the post-treatment visits was analyzed for mean changes from pre-treatment values, and a paired t-test was used to determine the significance of the changes. An analysis of variance was used to compare the two treatment groups, with respect to the mean changes from baseline.

Joint Heat, Effusion and Lameness Grade

Joint heat, effusion and lameness grade were significantly ($p<0.01$) reduced at weeks 1 and 2 compared to pre-treatment values in both the Synacid and Hylartin V treated horses.

Between weeks 1 and 2, Synacid treated horses showed further reduction in joint heat and effusion, whereas the Hylartin V horses did not undergo much change after week 1. With respect to lameness, both Synacid and Hylartin V treated horses showed progressive improvement between weeks 1 and 2.

The analysis of variance revealed no difference ($p>0.05$) between Synacid and Hylartin V, in their respective ability to reduce joint heat, joint effusion, and lameness.

The mean scores and mean changes from pre-treatment values for heat, effusion and lameness grade are provided in Table 13. The third column gives the p-value resulting from the treatment group comparison.

TABLE 13

Positive Controlled Field Study:
Results of Joint Heat, Effusion and Lameness Analysis at
Weeks 1 and 2 after Drug Treatment

| Variable | Synacid Score | Synacid Change from Pre-treatment | Hylartin V Score | Hylartin V Change from Pre-treatment | p - value treatment g comparison |
|---|---|---|---|---|---|
| Heat | | | | | |
| Week 1 | 1.4 | −0.55** | 1.2 | −0.61** | n.s |
| Week 2 | 1.0 | −0.96** | 1.1 | −0.63** | n.s |
| Effusion | | | | | |
| Week 1 | 1.2 | −0.45** | 1.1 | −0.62** | n.s |
| Week 2 | 1.0 | −0.59** | 1.2 | −0.52** | n.s |
| Lameness | | | | | |
| Week 1 | 1.6 | −0.97** | 1.6 | −0.82** | n.s |
| Week 2 | 1.3 | −1.17** | 1.4 | −1.11** | n.s |

**significantly lower than pre-treatment values, $p \leq 0.01$
n.s. nonsignificant, $p > 0.05$

Joint Size

Joint circumferences were analyzed for all horses with abnormal, or soft tissue swellings in their joints. Measurements were taken on treated and control joints at each evaluation. Changes from pre-treatment values were calculated for treated and for contralateral sound joints. The differences were considered as the meaningful joint changes and were analyzed with a paired t-test to establish significance. An analysis of variance was used to compare Synacid with Hylartin V.

The results are summarized in Table 14.

TABLE 14

Positive Controlled Field Study:
Joint Circumference Analysis

| | Difference between change from baseline of treated and untreated joints | | p - value of treatment group comparison |
|---|---|---|---|
| Evaluation | Synacid | Hylartin V | |
| Week 1 | −0.53** | −0.08 | n.s. |
| Week 2 | −0.68** | −0.45* | n.s. |

*significantly lower than pre-treatment values, $p \leq 0.05$
**significantly lower than pre-treatment values, $p \leq 0.01$
n.s. nonsignificant, $p > 0.05$ Synacid treated horses with soft tissue swelling experienced a greater decrease in joint circumference at weeks 1 and 2 than did Hylartin V group. The difference between the treated and control joints with respect to change from pre-treatment joint circumference was −0.53 at week 1, and −0.68 at week 2 in the Synacid group. Both of these values were statistically significant, (p≦0.01). The corresponding values for Hylartin V group were −0.08 at week 1 and −0.45 at week 2, with only the latter figure being significantly (p≦0.05) lower than prior to treatment. However, the analysis of the changes between the Synacid and the Hylartin V treated horses was not statistically significant (p>0.05).

Subjective Evaluation

Overall response to treatment was subjectively evaluated by the veterinarians as either "good", "fair", or "poor". Treatment failures were counted as those horses who were rated as having a "poor" response at the end of 2 weeks. Twenty-eight Synacid and 26 Hylartin V treated horses were categorized at the end of the study. In the "good" category there were 19 Synacid and 18 control drug horses. The "fair" category had 8 Synacid and 5 Hylartin V horses. Only 4 horses were considered as treatment failures or "poor" responses, including 1 Synacid and 3 Hylartin V treated horses. The statistical comparison of the treatment groups showed no significant difference between overall responses to treatment, p=0.44.

There were 14 horses in each drug group that were reinjected at one week following the initial treatment. Repeat injections at one week tended to relate to practice preference more than to the condition of the joints.

Synovial Fluid Analysis

Horses with elevated synovial fluid protein (≧10 mg/ml) and reduced synovial fluid viscosity (≦22) were included in the analysis of these two parameters. For each parameter equivalence between the Synacid and Hylartin V treatment groups was established prior to treatment. Statistical analysis of protein and viscosity data were based on mean percent changes from baseline.

Reductions in synovial fluid protein and increases in viscosity are considered to be the desirable changes.

Both treatment groups had decreased synovial fluid protein at weeks 1 and 2, compared to pre-treatment levels. However, only one of the changes was statistically different than baseline, (p≦0.05), that experienced by the Hylartin V group at week 1.

No statistical difference was found between the effects of Synacid and the effects of the Hylartin V on synovial fluid protein, p>0.05.

The mean percent changes in synovial fluid viscosity were not significantly different from pre-treatment values at week 1 or week 2, for either the Synacid or Hylartin V group. Synovial fluid viscosity is variable and prone to many physiological fluctuations. Therefore, these results are not surprising.

The treatment group comparison showed no significant difference between the effects of these two drugs on synovial fluid viscosity.

Table 15 summarizes the results of the synovial fluid analysis for protein and viscosity.

TABLE 15

Positive Controlled Field Study: Synovial Fluid Protein and Viscosity

| Parameter | Mean Scores | |
|---|---|---|
| | Synacid | Hylartin V |
| Protein | | |
| Pre-treatment | 15.18 (n = 17) | 14.88 (n = 13) |
| Week 1 | 12.97 (n = 13) | 12.64 (n = 13) |
| Week 2 | 14.34 (n = 7) | 12.29 (n = 7) |
| Viscosity | | |
| Pre-treatment | 6.82 (n = 32) | 6.42 (n = 30) |
| Week 1 | 4.80 (n = 27) | 6.68 (n = 30) |
| Week 2 | 4.69 (n = 11) | 4.65 (n = 12) |

| Parameters | Mean Percent Changes from Pre-Treatment | | p - value of treatment group comparison |
|---|---|---|---|
| | Synacid | Hylartin V | |
| Protein | | | |
| Week 1 | −12.80 | −14.33* | n.s. |
| Week 2 | −11.07 | −16.35 | n.s. |
| Viscosity | | | |
| Week 1 | −12.60 | 10.03 | n.s. |
| Week 2 | 17.06 | 0.54 | n.s. |

*significantly different than pre-treatment value, p ≦ 0.05
n.s. nonsignificant, p > 0.05

Results: Safety

Data from the 1, 3, and 5 day post-treatment follow-up visits was used to assess the safety of the two drugs used in this study. None of the horses experienced adverse side effects as a result of treatment. There were only 7 instances (4 Synacid and 3 Hylartin V) in which clinical signs were slightly exacerbated within 48 hours of treatment. All 7 cases were classed as transient and minor changes, and resolved spontaneously within 24 to 96 hours.

These effects can be anticipated following any intra-articular procedure.

4. Corroborative Field Studies

The purpose of this field trial was to evaluate the effectiveness of Synacid in a variety of joints with osteoarthritis and under conditions of use encountered in the field.

Horses received a full pre-treatment clinical and radiographic evaluation to obtain the diagnosis of joint disease. Horses with intra-articular fractures (except chip fractures) and septic joint were not admitted into the study.

A total of 397 joints (carpus=156, fetlock=117, hock=113, stifle=8, coffin=3) were treated in 236 horses and filed on 375 case report forms. Twenty-three horses were introduced into the study as new cases sometime over the two year study duration. Thus, there were 259 cases studied.

The majority of cases treated were racing Standardbreds (207) and racing Thoroughbreds (152). Among the remaining 38 horses, there were show jumpers, event horses and 20 working Quarterhorses. The average age of horses in this study was 4.9 years old. There were 132 females, 90 males, 170 geldings, and 5 undetermined. In 205 cases, the left limb was affected and in 192 cases the right limb was affected.

The difference between the number of horses treated (236) and the number of joints treated (397) is due to the incidence of bilateral or multiple joint problems in one horse. Unilateral joint dysfunction was present in 136 animals. In the remaining 100 animals some form of multiple dysfunction was present and more than one joint was injected.

| Case Reports Filed | Horses Treated | Separate Joints Treated |
|---|---|---|
| 136 | 136 | 136 |
| 189 | 98 | 211 |
| 50 | 25 | 50 |

| -continued | | |
|---|---|---|
| Case Reports Filed | Horses Treated | Separate Joints Treated |
| 375 | 259 | 397 |

Treatments consisted of intra-articular injection of 50 mg (5 ml) of Synacid 10 mg/ml, which is the labelled dose. Some exceptions occurred in hock joints, in which the total dose (50 mg or 5 ml) was occasionally divided between two small joint spaces, such as the distal intertarsal and tarsometatarsal spaces.

A second injection was optional at two weeks, if the veterinarian felt that response was not optimal.

Data was gathered in two trial formats. Series A involved 4 follow-up post-treatments, at 1, 2 and 4 weeks and at 3 months. Series B data was collected weekly for 6 consecutive weeks post-treatment. The two week and four week data from each series were combined for analysis of efficacy.

Observations

The following parameters were ranked by the veterinarians during the horses initial and follow-up visits:
1. Joint Heat: 0=Absent; 1=slight;
2. Joint Swelling: 2=moderate;
3. Excessive Fluid: 3=severe.
4. Pain on Flexion: present=yes; absent=no
5. Pain on Palpation: present=yes; absent=no
6. Functional Disorder (Lameness):
   1. Horse is racing/performing sound.
   2. Symptoms present only during extreme stress or work.
   3. Symptoms present only when in motion and when joint used, but not while standing.
   4. Symptoms present when standing and refusing to place full weight on joint under any condition.

Results

Results were analyzed for the combined number of joints (397) as well as separately for carpal joints (156) and fetlock joints (17), since the latter two joints were studied extensively in pivotal efficacy studies.

In the case of swelling, heat, excessive fluid and functional disorder, mean scores were lower at 2 and 4 weeks than prior to treatment. A statistical analysis using a paired t-test determined that each of these changes was a significant improvement ($p \leq 0.01$) compared to pre-treatment values.

For pain on flexion and pain on palpation, McNemar's test was used to compare the number of joints which went from having pain to not having pain, with the number of joints which went from not having pain to having pain. At two weeks and four weeks following Synacid treatment, a statistically significant ($p \leq 0.01$) number of horses were found to have improved with respect to pain on flexion and pain on palpation.

These results on lameness related variables are summarized in Table 16. Under the categories of pain on flexion and pain on palpation, the values listed in Table 16 are the actual number of horses, and percent of horses in parentheses, that were abnormal (had a "yes" response) prior to treatment, and the number of horses and percent of horses in parentheses that improved at weeks 2 and 4. The remaining values are given as mean scores.

A final performance evaluation was completed at the last follow-up visit, corresponding to 6 weeks in Series A and 90 to 120 days in Series B. Categories for final performance evaluation were:

Good: Horse resumed same level of activity as prior to treatment and remained racing sound for at least 3 months.

Fair: Resumed same or slightly lower level of activity/performance as prior to treatment but symptoms returned in less than 3 months.

Poor: Horse continued lame and/or unable to perform within 2 weeks of second treatment with Synacid.

Results of final performance evaluation were tabulated as number of horses (and percent of horses) in each category (good, fair, poor). Total improvement was taken as the sum of "good" and "fair" responses.

Of 187 joints evaluated in Series A, 117 (63%) were rated as "good" and 60 (32%) were rated as "fair", yielding an improvement of 177 or 95%. Ten cases (5%) were evaluated as "poor".

Series B final performance evaluation data on 149 joints was similar, with 98 cases (66%) in the "good" category, 50 (33%) in the "fair" category and 1 horse (1%) in the "poor" category. Total improvement in Series B was 148 cases, or 99%.

Therefore, a single intra-articular injection of Synacid was found to have a beneficial effect on performance as long as 90 days after treatment.

These results are summarized in Table 17.

TABLE 16

Corroborative Field Study:
Table of Means of Response Parameters

| Exam | Joint Swollen+ | Joint Hot+ | Excessive Fluid+ |
|---|---|---|---|
| All Joints | | | |
| Baseline | 0.8 | 0.5 | 1.1 |
| 2 Weeks | 0.5** | 0.1** | 0.4** |
| 4 Weeks | 0.4** | 0.1** | 0.3 |
| Carpus | | | |
| Baseline | 0.9 | 0.6 | 1.0 |
| 2 Weeks | 0.6** | 0.2** | 0.5** |
| 4 Weeks | 0.5** | 0.1** | 0.4** |
| Fetlock Joint | | | |
| Baseline | 1.1 | 0.6 | 1.4 |
| 2 Weeks | 0.5** | 0.2** | 0.6** |
| 4 Weeks | 0.4** | 0.1** | 0.6** |

| Exam | Functional Disorder+ | Pain On Flexion++ | Pain On Palpation++ |
|---|---|---|---|
| All Joints | | | |
| Baseline | 2.6 | 281 (71)[1] | 210 (53) |
| 2 Weeks | 1.8** | 164 (61)** | 114 (56)** |
| 4 Weeks | 1.6 | 206 (79)** | 141 (73)** |
| Carpus | | | |
| Baseline | 2.6 | 87 (56) | 102 (65) |
| 2 Weeks | 1.8** | 62 (75)** | 53 (54)** |
| 4 Weeks | 1.6** | 71 (88)** | 69 (77)** |
| Fetlock Joint | | | |
| Baseline | 2.7 | 111 (95) | 40 (34) |
| 2 Weeks | 1.9** | 50 (47)** | 24 (60)** |
| 4 Weeks | 1.6** | 69 (68)** | 26 (68)** |

**significantly different ($p \leq 0.01$) from pre-treatment
+statistical analysis based on paired t-test
++statistical analysis based on McNemar's test
[1] number (percent) of horses abnormal at baseline, and number (percent) improved at weeks two and four

TABLE 17

Corroborative Field Trial:
Summary of Final Performance Evaluation by Study Duration

| Category | n = 187 Series A | n = 149 Series B | Total |
|---|---|---|---|
| Good | 117 (63)* | 98 (66) | 215 (64) |

TABLE 17-continued

Corroborative Field Trial:
Summary of Final Performance Evaluation by Study Duration

| Category | n = 187 Series A | n = 149 Series B | Total |
|---|---|---|---|
| Fair | 60 (32) | 50 (33) | 110 (33) |
| Poor | 10 (5) | 1 (1) | 11 (3) |
| Total Improvement | 177 (95) | 148 (99) | 325 (97) |

*values are number (percent) of horses

The final performance evaluation was comparable in carpal and fetlock joints. The total improvement (good and fair responses) was 98% and 94% in carpi and fetlock joints respectively, as indicated in Table 18.

TABLE 18

Corroborative Field Trial:
Summary of Final Performance Evaluation by Joint

| Category | n = 129 Carpus | n = 101 Fetlock Joint |
|---|---|---|
| Good | 80 (62)* | 67 (66) |
| Fair | 47 (36) | 28 (28) |
| Poor | 2 (2) | 6 (6) |
| Total Improvement | 127 (98) | 95 (94) |

*values are number (percent) of horses

Eleven joints were rated as "poor" or treatment failure on the final performance evaluation. This represents 3% of the total joints treated. Two of the treatment failures were carpal joints, representing approximately 2% of the 129 carpi, and six (approximately 6%) were fetlock joints. The 11 treatment failures occurred in 9 horses and were reported by four of the investigators. Most treatment failures underwent improvement in at least one abnormal clinical sign. However, in these cases functional disorder did not improve substantially with the resolution of other clinical signs.

Results: Safety

No untoward reactions occurred as a result of treatment, except such as can be expected following routine joint invasion. Six (2.5%) of the 236 horses treated experienced minor drug related side effects (such as transient increases in heat or effusion) and 4 horses (1.7%) experienced reactions in which increased lameness was also a component. Lameness in these 4 horses resolved rapidly with adjunctive therapy. All reactions were reversible and none were associated with systemic signs or joint sepsis.

II. Comparative Efficacy

The purpose of the clinical trials discussed herein was to study the relationship between molecular weight and therapeutic efficacy of sodium hyaluronate. A disease model of induced adjuvant carpitis was preferred as the experimental design because of its consistency, reproducibility, objectivity and relationship to the naturally occurring disease.

Eighteen horses were randomly allocated to one of three treatment groups of 6 horses each. Group I received sodium hyaluronate average molecular weight 75,000; Group II received sodium hyaluronate average molecular weight 150,000; and Group III received sodium hyaluronate average molecular weight 2 million.

The treatment administrations and clinical evaluations were performed by two different veterinarians to insure a blind test.

Response variables associated with joint inflammation and dysfunction as well as general health were evaluated prior to model induction, prior to the designated treatment, and weekly for 4 weeks post treatment.

Physical examination and statistical analysis of the data did not reveal a difference between the three treatment groups with respect to resolution of the clinical signs caused by model induction.

The conclusion is that molecular weight of sodium hyaluronate is not related to therapeutic drug efficacy in adjuvant induced carpitis in the horse.

Methodology

An induced adjuvant carpitis in horses was selected as the model by which to study the relationship between molecular weight and clinical efficacy of sodium hyaluronate. This arthritis model has been previously described in the test entitled "Synacid Dose Response and Efficacy Study and Comparative Efficacy Study between Synacid and Hylartin V in Equine Adjuvant Carpitis Model". The study was blinded in that one veterinarian administered the randomized treatments, while a second veterinarian performed the evaluations.

Three treatment groups were used based on different molecular weights of sodium hyaluronate as follows:

Group I: 50 mg Synacid (L23021) molecular weight 75,000;

Group II: 50 mg Synacid (L23028) molecular weight 150 000;

Group III: 20 mg Hylartin V (L KE40453) molecular weight 1-3 million.

The study was performed in two replicates in which nine horses were randomly assigned to one of these three test groups. Therefore, each test group was represented by three animals per replicate, or a total of 6 animals per group over the entire study period.

The following parameters were evaluated by physical examination or laboratory analysis prior to model induction, 5 days after model induction which coincided with the time of treatment, and weekly thereafter for 4 weeks:

a) radiocarpal joint circumference
b) angle of flexion of carpus at rest
c) maximum angle of flexion permitted upon manual manipulation
d) stride length at rest
e) stride length after controlled exercise
f) pain on palpation
g) lameness at the walk
h) hyperthermia of the affected joint
i) carpal volume
j) temperature, pulse and respiration
k) synovial fluid viscosity and protein content
l) complete blood count

Results

The statistical analysis examined group effects (dose effects) over the study duration as changes from baseline values. A separate analysis comparing differences among the individual horses in each group with differences between the groups was used to determine that the randomization sequence of the 3 test groups was not accidently biased by "luck of the draw". This replicate analysis reveals that 26 tests out of a total of 138 appeared significant. Four of these replicate differences occurred in the baseline period due to random horse selections.

Nine of these occurrences of replicate significance arose for variables in which no clinical significance can be attached to the findings; for example, in the differential while blood cell counts, respiration and pulse. Seven of these "replicate differences" occurred for parameters whose baseline values also showed a replicate difference. Hence, no clinical significance can be attached to these findings.

No responses showed sequential replicate efforts over the entire study period. Protein showed a replicate effect for the last 3 observation periods, which may be attributed to random error based on the general scattering of the replicate significant occurrences or could be interpreted as a real event. The mean protein values for the three dose groups in the second replicate at days 21 and 28 are almost half of the protein values for the three dose groups in the first replicate. Our clinical interpretation is that protein values spontaneously decreased in the second replicate compared to the first. This inconsistent behaviour of protein is not surprising since the adjuvant model dose response study (submitted to INAD 2675) revealed the same phenomenon. We, therefore, conclude that the two replicates were in fact equivalent with respect to all measured responses except for synovial fluid protein, where the differences, if real, are not related to the case selection.

There were 10 instances of dose effects out of a total possibility of 115. All of these 10 instances of dose effect compared to baseline occur for parameters of no clinical consequence: respiration, 4; pulse, 2; percent lymphocytes, 1; percent basophils, 2; and percent neutrophils, 1.

Dose X replicate effects were significant in only 4 out of 115 tests, which is fewer than that expected by chance alone.

The three molecular weights of sodium hyaluronate used in this study were clinically indistinguishable with respect to resolution of the signs of inflammation and pain produced by the carpitis model. No adverse effects occurred as a result of treatment with any of the three groups used, as supported by hematology and routine TPR's.

It was also observed that flexion at rest, maximum flexion permitted, stride length at rest and after exercise, pain on palpation, lameness, and hyperthermia all return to normal following treatment, and at the same time observation period for each of the three treatment groups. Thus, the treatment groups have equivalent efficacy for these responses.

Joint circumference did not return to pre-model induction measurements in any of the treatment groups. However, gradual improvement was consistent and parallel among the three treatment groups. Joint circumference exhibited the same pattern in the dose response study.

Synovial fluid protein decreased significantly from model induction levels in this molecular weight study, as well as uniformly among the three treatment groups. However, the interpretation is equivocal since synovial fluid protein content is naturally variable and the adjuvant carpitis model does not always persist for this variable.

No drug effects were noted on synovial fluid viscosity which remained at post-model induction levels even at 28 days after treatment. This was consistent for all three treatment groups. The logical explanation is that synovial membrane function was still impaired at the 28 day observation period, resulting in poorly aggregated hyaluronate within the joint fluid and, therefore, a concomitant low viscosity. It is interesting to note that the claim made by Pharmacia for Hylartin V suggests that this high molecular fraction of sodium hyaluronate functions to restore high viscosity to the synovial fluid. This claim is not borne out by the results of this adjuvant carpitis model.

Statistical analysis of carpal volume calculations also failed to reveal differences between the three molecular weight doses studied.

III. Safety and Efficacy of Synacid In Hock Joints Field Test

In a multicentre open field trial conducted in the United States to test the safety and efficacy of Synacid, 113 hock joints were treated by 9 equine veterinarians, with 90 cases coming from 2 veterinarians whose practises involve frequent diagnosis and treatment of hock lameness. Bilateral hock lameness was treated in 46 of the horses.

In addition to the studies on hock joints, 156 carpi, 117 fetlock joints, 8 stifles and 3 coffin joints were also treated with Synacid under the same study protocol.

Prior to treatment, horses were evaluated radiologically, and clinically for lameness, degree of heat, soft tissue swelling and effusion, and pain responses to flexion and digital palpation.

According to the protocol, horses with evidence or a previous history of joint sepsis, intra-articular fractures, and recent post-surgical cases were excluded from the study.

A repeat injection was made optional two weeks after the initial treatment, at the veterinarian's discretion.

Post-treatment observations were gathered in two trial formats. In Series A, there were 4 follow-up visits at 1 week, 2 weeks, 1 month, and 3-4 months. In Series B, there were 6 follow-up visits at weekly intervals post-treatment.

| | |
|---|---|
| 1. Joint heat | |
| 2. Joint swelling | 0 = Absent; 1 = Slight; |
| 3. Joint effusion | 2 = Moderate; 3 = Severe |
| 4. Pain on Palpation | present = yes; absent = no |
| 5. Pain on Flexion | |

Lameness was also ranked numerically using a standard scoring system:
1 = Horse is racing/performing sound
2 = Symptoms present only during extreme stress or work
3 = Symptoms present when in motion and when joint used, but not while standing
4 = Symptoms present when standing and refusing to place full weight on joint under any condition Statistical analysis of the quantitative data was performed using a t-test to determine if changes in clinical variables were significantly different at post-treatment intervals compared to pre-treatment with a Synacid treatment. Subjective variables (pain on palpation, pain on flexion) were analyzed by McNemar's test using a normal approximation. The 2 week and 4 week data of Series A and B were combined for this analysis.

The demographic variables for the 113 hock joints treated with Synacid are provided in Table 1. Mean age was 6.4 years and left and right hocks were equally involved. Racing Standardbreds were predominant among the breeds. The Thoroughbreds in the study were all show jumpers.

Ninety one cases had radiographic evidence of pathology, 10 were normal, and in 12 cases radiographic assessment was not available. The radiographic findings were generally indicative of degenerative joint disease and included: osteophytes (lipping, exostoses and spur formation), lytic lesions, narrowing of the joint space and subchondral bone lesions.

TABLE 1

Demographic Variables: Field Study of the Safety and Efficacy of Synacid in Hock Joints

| Age: | mean (years) | 6.4 |
|---|---|---|
| | Std. Dev. | 3.3 |
| | n | 108 |
| Breed: | Standardbred | 67 |
| | Thoroughbred | 34 |
| | Warmblood | 8 |
| | Quarterhorse | 3 |
| | Appaloosa | 1 |
| | n | 113 |
| Sex: | Female | 22 |
| | Male | 25 |
| | Geldings | 66 |
| | n | 113 |
| Side Affected: | left | 56 |
| | right | 57 |
| | n | 113 |
| Joint treated: | tibiotarsal | 113 |
| | tarsometatarsal | 55 |
| Unilateral: | | 67 |
| Bilateral: | | 46 |
| | n | 113 |
| X-rays: | normal | 10 |
| | abnormal | 91 |
| | n | 101 |

The tibiotarsal joint was treated in every case. Both the tibiotarsal and the tarsometatarsal joint were treated in 55 cases. In 11 of these cases, the 50 mg dose was divided between the two compartments, with the tibiotarsal receiving 30 mg (3 cc's) and the tarsometatarsal receiving 20 mg (2 cc's). In the remaining 44 multiple joint cases, a full dose (50 mg) was injected into the tibiotarsal joint, while the tarsometatarsal joint received between 20 and 50 mg additionally.

Table 2 provides the mean scores of the clinical parameters prior to treatment. The relatively low scores reflect that joint heat, swelling and effusion were not severe in these cases, which is a typical finding in hock joint lameness. The most consistent abnormality was a positive flexion response, which was present in 78 cases and absent in 35. Related to this, the mean lameness score was 2.6, indicating lameness at racing and training speeds, but not at rest.

TABLE 2

Pre-Treatment Clinical Scores in the Field Study of the Safety and Efficacy of Synacid in Hock Joints

| Response Variable | Mean Score (n = 113) |
|---|---|
| Joint Heat[a] | 0.33 |
| Joint Swelling[a] | 0.5 |
| Joint Effusion[a] | 0.9 |
| Lameness[b] | 2.6 |
| Pain on Flexion: | |
| present | 78 |
| absent | 35 |
| Pain on Palpation: | |
| present | 66 |
| absent | 47 |

[a]Maximum score possible = 3
[b]Maximum score possible = 4

Table 3 provides a comparison of the post-treatment and pre-treatment data for the clinical response variables. Changes in each category are statistically significant ($p \leq 0.01$) at both 2 and 4 weeks following Synacid treatment. Swelling, heat and effusion were virtually absent at the 4 week visit, while the lameness score of 1.5 reflected that most horses had returned to successful competition. Pain on digital palpation was still present in 19 cases at the end of 4 weeks, representing an improvement in 70% of the horses that manifested this clinical sign prior to Synacid treatment.

TABLE 3

Summary of Response Variables over Time: Field Study of the Safety and Efficacy of Synacid in Hock Joints

| Response Variable | Mean Scores at Evaluation Periods | | |
|---|---|---|---|
| | Pretreatment | 2 weeks | 4 weeks |
| Joint Swelling | 0.5 | 0.3* | 0.2* |
| Joint Heat | 0.33 | 0.03* | 0.01* |
| Joint Effusion | 0.9 | 0.2* | 0.1* |
| Lameness | 2.6 | 1.7* | 1.5* |
| Pain on Flexion[1] | 78 | 25* (68) | 14* (70) |
| Pain on Palpation[1] | 66 | 29* (57) | 19* (70) |

*Significantly ($p \leq 0.01$) different from pretreatment value
[1]Figures are for number of cases with signs present and percent improvement in parentheses.

Repeat injections were administered in 5 joints, or 4%. This figure is somewhat higher than the incidence of repeat injections in carpal joints (2%). Most likely the small difference in incidence of repeat injections between carpal and hock joints is a reflection of the individual practice style of veterinarians, rather than a difference in clinical response between joints.

Two horses were reported to have experienced post-treatment side effects including exacerbation of lameness. Each case resolved rapidly, without adjunctive therapy in one horse, and with Phenylbutazone therapy for 1 day in the other horse. Neither case was a treatment failure. Therefore, the side effects did not interfere with the beneficial outcome of Synacid treatment.

A subjective assessment of relative performance was made at the two and four week follow-up visits. Performance relative to the last evaluation was designated as either.

1. good: horse resumed racing and/or performing as well as prior to symptoms
2. fair: resumed to previous performance but not as well as immediately before onset of symptoms
3. poor: horse continued lame and/or unable to perform within 1-2 weeks of treatment The results are summarized in Table 4, which also provides the relative performance evaluations of the carpal joint cases. The data in Table 4 illustrates that improvement in performance was evident only 2 weeks after Synacid treatment, and that performance continued to improve between 2 and 4 weeks after treatment. Total improvement (the sum of good and fair responses) was 95 and 97 percent at weeks two and four, respectively.

Two horses (3 joints) were classed as treatment failures, based on a poor response at the final performance evaluation. These 3 cases represent 3% of the 113 hock joints treated. One horse was an eight-year-old Standardbred treated for degenerative joint disease of the right hock. The other horse was a four-year-old Thoroughbred with no radiographic lesions, who was treated for bilateral hock lameness. Both horses experienced some improvement in clinical signs. However, lameness did not decrease significantly or the decrease in lameness was only short-lived. Neither of these horses had benefited from a repeat injection.

TABLE 4

Performance Relative to the Last Evaluation: Field Study of the Safety and Efficacy of Synacid in Hock Joints

| Category | 2 Weeks[1] | | 4 Weeks[1] | |
| --- | --- | --- | --- | --- |
| | (n = 112) Hock | (n = 146) Carpus | (n = 109) Hock | (n = 134) Carpus |
| Good | 62 (55) | 78 (53) | 70 (64) | 80 (60) |
| Fair | 44 (40) | 60 (41) | 36 (33) | 48 (36) |
| Poor | 6 (5) | 8 (5) | 3 (3) | 6 (4) |
| Total Improvement | 106 (95) | 138 (94) | 106 (97) | 128 (96) |

[1]Each value represents the number of horses, and percent of horses in parentheses.

Improvement in performance was comparable in hocks and carpi at the recommended therapeutic dose of Synacid—50 mg/joint. Thus, the therapeutic dose of Synacid is constant among different joint types.

Return to competitive form is of paramount importance in evaluating the success of any treatment. The results of this study constitute substantial evidence of the resolution of hock lameness and the successful return to competition, following intra-articular injection of Synacid.

From the foregoing description, one skilled in the art can easily ascertain the essential characteristics of the invention and, without departing from the spirit and scope thereof, can make various changes and modifications of the invention and adapt it to various uses and conditions.

What is claimed is:

1. A method for the intra-articular treatment of animals, which comprises:

injecting a therapeutically effective dosage of a solution of a heat stable, purified, pyrogen-free, heat sterilized fraction of a sodium salt of hyaluronic acid having an average molecular weight within the range of 50,000 to 200,000 into a joint of an animal suffering from a degenerative joint disease, wherein said solution has a pH within the range of about 6.8-8.0 at 25° C., a specific absorbance of a 1% solution of 1.5 to 3, and comprises on a total weight basis:
(i) 97 to 102% sodium hyaluronate;
(ii) about 1% sulphated mucopolysaccharides;
(iii) about 0.4% albumin;
(iv) about 15 to 19% sulphated ash;
(v) about 2% sodium chloride; and
(vi) about 4% solvents selected from the group consisting of acetone, ethanol, and mixtures thereof;

a preservative comprising, per milliliter of final solution a mixture of 0.41 to 0.5 milligrams sodium benzoate, 0.86 to 1.2 milligrams methylparaben, and 0.043 to 0.06 milligrams propylparaben; and water in a dosage form containing said heat stable, purified, pyrogen-free, heat sterilized hyaluronic acid in an amount within the range of 10 mg/ml solution to 20 mg/ml solution.

2. A method for the intra-articular treatment of animals, which comprises:

injecting a therapeutically effective dosage of a solution of a heat stable, purified, pyrogen-free, heat sterilized fraction of a sodium salt of hyaluronic acid having an average molecular weight within the range of 75,000 to 150,000 into a joint of an animal suffering from a degenerative joint disease, wherein said solution has a pH within the range of about 6.8-8.0 at 25° C., a specific absorbance of a 1% solution of 1.5 to 3, and comprises on a total weight basis:
(i) 97 to 102% sodium hyaluronate;
(ii) about 1% sulphated mucopolysaccharides;
(iii) about 0.4% albumin;
(iv) about 15 to 19% sulphated ash;
(v) about 2% sodium chloride; and
(vi) about 4% solvents selected from the group consisting of acetone, ethanol, and mixtures thereof;

a preservative comprising, per milliliter of final solution, a mixture of 0.41 to 0.5 milligrams sodium benzoate, 0.86 to 1.2 milligrams methylparaben, and 0.043 to 0.06 milligrams propylparaben; and water in a dosage form containing said heat stable, purified, pyrogen-free, heat sterilized hyaluronic acid in an amount within the range of 10 mg/ml solution to 20 mg/ml solution.

3. A method for the intra-articular treatment of animals, which comprises:

injecting a therapeutically effective dosage of a solution of a heat stable, purified, pyrogen-free, heat sterilized fraction of a sodium salt of hyaluronic acid having an average molecular weight of about 150,000 into a joint of an animal suffering from a degenerative joint disease, wherein said solution has a pH within the range of about 6.8-8.0 at 25° C., a specific absorbance of a 1% solution of 1.5 to 3, and comprises on a total weight basis:
(i) 97 to 102% sodium hyaluronate;
(ii) about 1% sulphated mucopolysaccharides;
(iii) about 0.4% albumin;
(iv) about 15 to 19% sulphated ash;
(v) about 2% sodium chloride; and
(vi) about 4% solvents selected from the group consisting of acetone, ethanol, and mixtures thereof;

a preservative comprising, per milliliter of final solution, a mixture of 0.41 to 0.5 milligrams sodium benzoate, 0.86 to 1.2 milligrams methylparaben, and 0.043 to 0.06 milligrams propylparaben; and water in a dosage form containing said heat stable, purified, pyrogen-free, heat sterilized hyaluronic acid in an amount within the range of 10 mg/ml solution to 20 mg/ml solution.

4. A method for the intra-articular treatment of animals, which comprises:

injecting a therapeutically effective dosage of a solution of a heat stable, purified, pyrogen-free, heat sterilized fraction of a sodium salt of hyaluronic acid having an average molecular weight of about 75,000 into a joint of an animal suffering from a degenerative joint disease, wherein said solution has a pH within the range of about 6.8-8.0 at 25° C., a specific absorbance of a 1% solution of 1.5 to 3, and comprises on a total weight basis:
(i) 97 to 102% sodium hyaluronate;
(ii) about 1% sulphated mucopolysaccharides;
(iii) about 0.4% albumin;
(iv) about 15 to 19% sulphated ash;
(v) about 2% sodium chloride; and
(vi) about 4% solvents selected from the group consisting of acetone, ethanol, and mixtures thereof;

a preservative comprising, per milliliter of final solution, a mixture of 0.41 to 0.5 milligrams sodium benzoate, 0.86 to 1.2 milligrams methylparaben, and 0.043 to 0.06 milligrams propylparaben; and water in a dosage form containing said heat stable, purified, pyrogen-free, heat sterilized hyaluronic acid in an amount within the range of 10 mg/ml solution to 20 mg/ml solution.

* * * * *